United States Patent [19]

Jaffe

[11] Patent Number: 4,822,358
[45] Date of Patent: Apr. 18, 1989

[54] INTRAOCULAR LENS

[75] Inventor: Norman S. Jaffe, N. Miami Beach, Fla.

[73] Assignee: Cilco, Inc., Bellevue, Wash.

[21] Appl. No.: 150,460

[22] Filed: Feb. 1, 1988

Related U.S. Application Data

[63] Continuation of Ser. No. 8,056, Jan. 16, 1987, abandoned, which is a continuation of Ser. No. 744,137, Jun. 12, 1985, abandoned.

[51] Int. Cl.$^4$ .............................................. A61F 2/16
[52] U.S. Cl. ......................................................... 623/6
[58] Field of Search ............................................. 623/6

[56] References Cited

PUBLICATIONS

Cilco Lens Style Sheet, May 1983.
"Lens Styles From Cilo," Cilco Lens Co.; Oct. 1982, Lens Styles AR-4 and SK-4.

*Primary Examiner*—Richard J. Apley
*Assistant Examiner*—James Prizant
*Attorney, Agent, or Firm*—Pravel, Gambrell, Hewitt, Kimball & Krieger

[57] ABSTRACT

A lens implant for insertion in a human eye after an extra-capsular extraction includes a lens body of polymethyl methacrylate to which are attached first and second curved holding loops formed integrally with and projecting from the periphery of the lens. The loops are diametrically attached to the lens and the loops project from the lens along a curved path so that the pair of loops define generally an ellipse that symmetrically surrounds the lens body. Each loop terminates at a free end in a positiion near the point of attachment of the other loop. The free end of one loop and the point of attachment of the second loop are in a common quadrant of the ellipse, with the respective ellipse quadrant having a loop-free end and a point of attachment being also diagonally opposed. The free end of one loop and the point of attachment of the second loop are radially spaced by a measure of less than ninety degrees (90°). The improved design provides a better geometric profile for surgical insertion in combination with improved flexibility characteristics.

7 Claims, 1 Drawing Sheet

INTRAOCULAR LENS

This is a continuation of co-pending application Ser. No. 007,056 filed on 1/16/87 (abandoned), which is a continuation of application No. 06/744,137 filed on 6/12/85 (abandoned).

BACKGROUND OF THE INVENTION

The present invention relates to lens implants or intraocular lenses (IOL's) that are used to replace a patient's natural lens after it has been surgically removed. More particularly, the invention relates to an IOL with a unique haptic or loop configuration that is stiff enough to provide sufficient stability for holding the lens in place after implantation, but is flexible enough to facilitate insertion with no residual negative effects to the patient.

There are many IOL's of varied designs on the market that are used to replace the natural lens after what is known as extra-capsular surgery where the natural lens of the eye is surgically removed. Such lenses include an optical portion or lens and "loops" or "haptics" that retain the optical portion in the eye either anteriorly or posteriorly relative to the iris. The lens that is the subject of the present invention is preferably a posterior chamber, one-piece lens formed of polymethylmethacrylate (e.g., PMMA) or other suitable bio-compatible material, although the same configuration could be used on a three-piece lens where the loops are formed separate from the optic portion and attached to it. In such lenses, the optic portion could be formed of PMMA and the loops of material such as polypropylene.

The optic portion of the lens replaces the natural lens of the eye that has been removed and operates to focus the image discerned by the eye on the retina located on the back wall of the posterior chamber. The loops or haptics project from the periphery of the optic portion and operate to hold the lens in its position within the eye. The degree of flexing and configuration of haptic are important because they determine the characteristics of the loop for holding the IOL in place and also accommodate the constantly changing configuration or shape of the eyeball during the wearer's daily activities.

An IOL is normally inserted through an incision formed by the surgeon at the junction of the corneal and sclera. Various insertion techniques have been developed for minimizing the size of the incision such as, for example, having loops that are flexible enough to be pressed inwardly or by manipulating the loops through the incision and rotating the lens so that the incision need not be any wider than the diameter of the optic portion. The loops are usually in the form of thin, curved arms having a free end. Many IOLs include openings at both ends of the loop or in the outer periphery of the optic portion for accommodating a surgical instrument to aid in implantation.

A number of IOL lens designs have been proposed and used in the past. The acceptability of many of such configurations often times depends on physician preference, but physical characteristics play an important role in determining patient comfort and ease of implantation. One example of a single-piece IOL that has been developed is taught in U.S. Pat. No. 4,476,591 to Arnott, issued Oct. 16, 1984. This lens, while generally similar in design in the subject invention, includes loops that extend well beyond the beginning of the other loop and are believed to be more flexible than desirable. On the other hand, there are lenses such as the one known as the C-loop lens that does not include any portion of the loop spaced radially outward from the periphery of the optic portion and includes loops that terminate far short of the beginning of the next loop and therefore does not provide the flexibility characteristics that many consider to be desirable.

Ideally, the loops or haptics need to provide compressive forces that are great enough to hold a lens in place, but not great enough to exert undue pressure inside the eye. Further, the loops must be stable enough so that as the shape of the eyeball changes, there should be no significant change in lenticular displacement upon compression, nor should descentration (transverse displacement) occur upon compression. Another characteristic is to determine whether the lens tilts in any way during compression.

Balanced against these considerations are whether lenses can be equally locatable within the eye because of the location of positioning holes in similar portions of the lens. Once in the eye, the lens should be able to resist rotational forces within the eye and remain relatively stable throughout the range of changes in the shape of the eyeball. Further, the profile of the lens including the outer periphery of the lens must be considered in order to determine the optimum size of incision for accommodating the lens. Obviously, the larger the required incision the less advantageous the lens.

SUMMARY OF THE INVENTION

An IOL has been developed that has loops that are believed to provide the ideal flexibility without sacrificing stability in the eye. Further, the loops are compressible during insertion and the lens can be manipulated such that only a relatively small incision for insertion is necessary.

The subject lens, like all IOLs, includes an optic portion and a pair of curved holding loops that project from the periphery of the optic portion at points of attachment that are substantially diametrically opposite each other. The loops are curved to define generally an ellipse with narrower and wider sides that symmetrically surround the optic portion.

Each loop includes a first segment extending substantially radially outward from the optic portion with a sharp bend extending from the first segment. A second segment extends from the bend and includes a portion that is spaced radially outward from the periphery of the optic portion, the second segment forming a portion of one of the narrower sides of the ellipse and providing a cantilevered connected with the optic portion. A third segment extends from the second segment and has a greater curvature than the second segment and forms a portion of one of the wider sides of the ellipse. The end of the third segment remote from the second segment is free and lies radially outward of the optic portion along a radial-line that is in close proximity to the beginning of the first segment of the other loop. This design provides a pair of loops with first segments that are relatively stiff and other segments that are more flexible.

The lens can be formed as a single-piece lens of PMMA and can have openings in the first segment or at the free end of each loop to aid in manipulating and inserting the lens.

BRIEF DESCRIPTION OF THE DRAWINGS

In order to obtain a better understanding of the invention, the following drawings should be considered in conjunction with the detailed disclosure of an exemplary embodiment set forth below.

DETAILED DESCRIPTION OF AN EXEMPLARY EMBODIMENT

Figure 1:
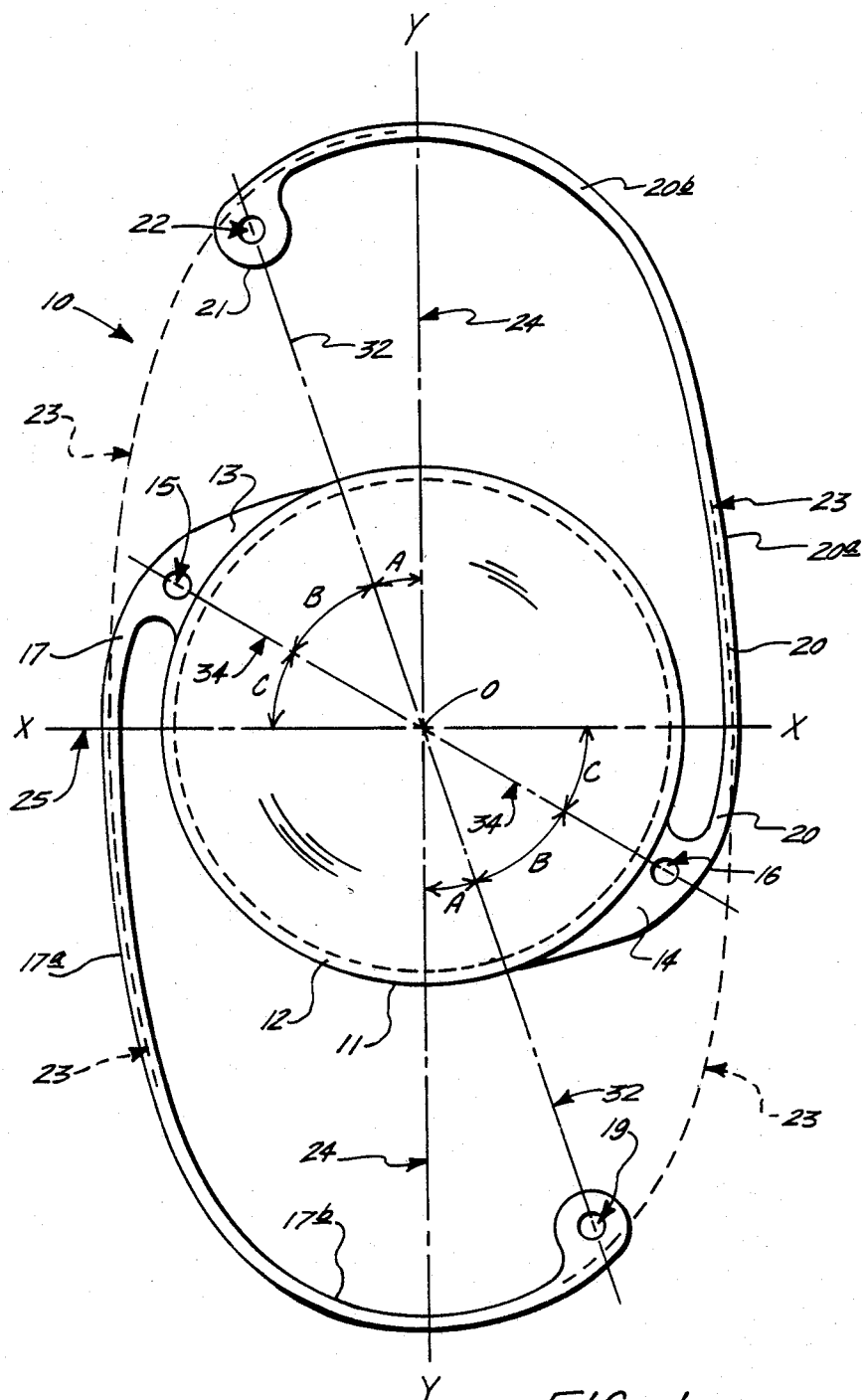
FIG. 1 is a front plan view of a lens made in accordance with the present invention.
Figure 2:
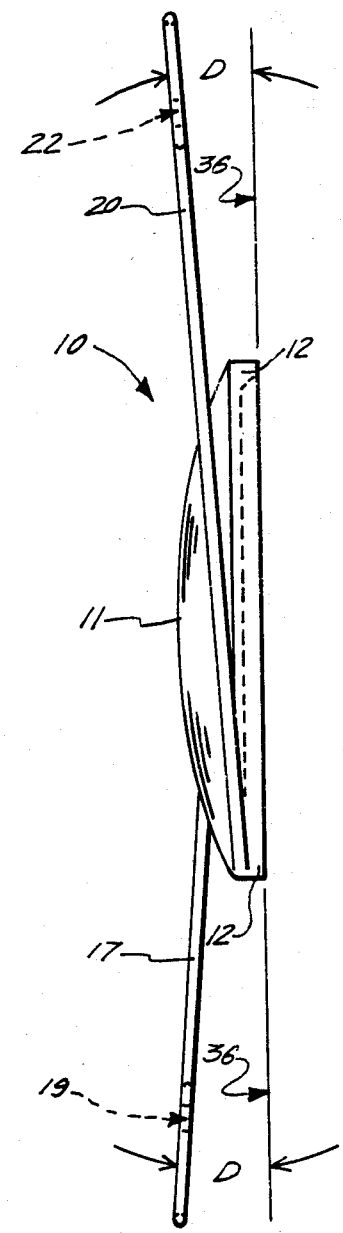
FIG. 2 is a side view of the lens shown in FIG. 1.

FIGS. 1 and 2 illustrate an exemplary embodiment of the IOL of the present invention that is designated generally by reference numeral 10. The IOL 10 is formed as a single-piece lens, that is, it includes a lens body 11 and a pair of loops or haptics designated by reference numerals 17, 20, formed integral with each other of a single piece of material. The lens is preferably formed of polymethylmethacrylate (PMMA) or other suitable bio-compatible material. The loops 17, 20 are attached to the lens body 11 at a peripheral edge 12 through first segments 13, 14 that respectively include openings 15, 16 for allowing the IOL to be manipulated during implantation by the surgeon with appropriate instruments.

The first segments 13, 14 extend substantially radially outward from the lens body 11 and end in a sharp bend on the side opposite the attachment with the peripheral edge 12. The loops 17, 20 further include respective second segments 17a, 20a that project from the bends in the first segments 13, 14. The second segments 17a, 20a are spaced radially outward from the peripheral edge 12 and form slots S between the peripheral edge 12 and the second segments 13, 14 to provide a cantilevered attachment between the loops 17, 20 and the optic portion 11.

The loops 17, 20 further include third segments 17b, 20b, respectively, that have a greater curvature than the second segments 17a, 2a. As shown best in FIG. 1, the loops 17, 20 in combination define a generally elliptical path 23 that symmetrically surrounds the optic portion 11. The elliptical path 23 is shown generally by the combination of a dotted line 23 and the shape of the loops 17, 20. The elliptical 23 includes narrower and wider sides, the second segments 17a, 20a forming a portion of the narrower sides of the ellipse, while the third segments 17b, 20b form a portion of the wider sides of the ellipse. The elliptical path 23 is graphically illustrated as having intersecting, horizontal and vertical axes X, Y, respectively, that divide the path 23 into four quadrants. As shown in FIG. 1, the X axis is identified by reference numeral 25 and the Y axis by reference numeral 24.

As shown, the ends of the third segments 17b, 20b form free ends 21 of the loops and lie radially outward of the optic portion 11 along a radial line 32 that is in close proximity to the beginning of the first segments 13, 14, the free end 21 of one loop and the first segment 13 of the other loop being located in a common quadrant of the ellipse 23. As shown, each free end 21 is radially spaced by an angle of about 50° from the center line of the openings 15, 16 in the first segments 13, 14. This angle is designated by reference letter B. The angle identified by letter A indicates that the radial line 32 is spaced from the Y axis 24 by an angle of about 18°-20° and the radial line intersecting the openings 15, 16, is spaced from the X axis 25 by an angle C that is about 20°-22°.

By forming the loops 17, 20 with second segments 17a, 20a a spaced radially outward from the peripheral edge 12, the loops are sufficiently flexible enough to allow them to be pressed inward during implantation and to accommodate internal shape changes within the eyeball. However, by terminating the loops 17, 20 so that their free ends lie along the radial line 32 they are not as flexible as, for example, lenses where the free ends extend significantly beyond the point where the first segments 13, 14 are attached to the peripheral edge 12.

Referring to FIG. 2, each loop 17, 20 is formed at an angle D relative to the plane of the posterior side of the optic portion 11. This angulation of about 10° is designed to place the lens optic against the capsular bag and away from the iris of the eye. A ridge 12 is formed on the posterior side of the optic portion 11 for holding the posterior capsule of the eye away from the posterior lens surface.

The foregoing description of the invention is intended to be illustrative and explanatory and various changes in the size, shape and materials, as well in the improvements to the invention may be made without departing from the spirit of the invention as defined in the appended claims.

I claim:

1. An intraocular lens comprising:
   (a) an optic having a periphery;
   (b) first and second haptics of substantially similar geometry, each connected to and projecting from the periphery of the optic on substantially diametrically opposite sides from each other;
   (c) the haptics being curved to define generally an ellipse, such that the haptics and the defined ellipse encircle the optic with narrower ellipse sides along an X axis and wider ellipse sides along a Y-axis, the X and Y ellipse axes traversing respectively the narrowest and widest portions of the ellipse, defining four ellipse quadrants;
   (d) each haptic including a first gusset segment extending radially outwardly from said optic periphery and a relatively long, thin, loop portion projecting from the gusset segment, at a beginning position;
   (e) each loop portion including a second segment extending from the first gusset segment and spaced outwardly from the periphery of the optic, the second segment including a first portion extending from the gusset segment and generally parallel to the periphery of the optic for a distance the second segment further including at least one second portion with a substantially greater curvature than the optic periphery extending from the first portion and through at least one-half of an ellipse quadrant, so that the second loop segment projects away from the optic to a point that is substantially farther from the optic than the beginning position, the second segment forming at least a portion of one of the narrower sides of the ellipse;
   (f) each haptic further including a third segment extending from the second segment and having a significantly smaller radius of curvature than the second portion and forming at least a major portion of one of the narrower sides of the ellipse;
   (g) the third segment of each haptic terminating at a free end lying outward of the optic portion along a line extending radially from the optic portion that is positioned relative to the beginning of the second segment of the other haptic so that the free end of one haptic approaches but does not overlap the second segment of the other haptic when the haptics are in an uncompressed state; and (h) wherein the first segment of the haptics are relatively stiff and the other segments being more flexible.

2. The intraocular lens of claim 1, wherein said lens is formed of a single-piece of polymethylmethacrylate.

3. The intraocular lens of claim 1, wherein the free end of each loop falls in the same quadrant as the first segment of the other loop.

4. The intraocular lens of claim 1, wherein the free ends include rounded portions, the center of the rounded portions falling along said radial line.

5. The intraocular lens of claim 1, wherein said radial line is located at approximately 20°-22° relative to the Y axis of the ellipse.

6. The intraocular lens of claim 1, wherein said radial line is located approximately 50° relative to a second radial that passes through the center of said first segment.

7. The intraocular lens of claim 1, wherein the portion of said second segment that is spaced radially outward from the periphery of the optic portion forms a slot between said second segment and the optic portion that extends throughout the quadrant of the first segment.

* * * * *